United States Patent [19]

Hsieh

[11] 4,317,745

[45] Mar. 2, 1982

[54] CATALYTIC OXIDATION OF PHENOLS TO 1,4-BENZOQUINONES

[75] Inventor: Hsin H. Hsieh, Baton Rouge, La.

[73] Assignee: The Dow Chemical Company, Midland, Mich.

[21] Appl. No.: 216,107

[22] Filed: Dec. 15, 1980

[51] Int. Cl.³ .............................................. C07C 49/66
[52] U.S. Cl. .................................. 252/428; 252/430; 252/432; 260/396 R
[58] Field of Search ....................... 252/432, 428, 430

[56] References Cited

U.S. PATENT DOCUMENTS

| | | | |
|---|---|---|---|
| 2,765,323 | 10/1956 | Dixon et al. | 260/396 |
| 2,815,352 | 12/1957 | Johannsen et al. | 260/346.4 |
| 2,863,884 | 12/1958 | Tribit et al. | 260/396 |
| 2,956,065 | 10/1960 | Walt et al. | 260/396 |
| 3,038,911 | 6/1962 | Berets et al. | 260/346.4 |
| 3,095,430 | 6/1963 | Wetistein | 260/396 |
| 3,232,955 | 2/1966 | Neunenmacher et al. | 260/346.4 |
| 3,402,187 | 9/1968 | Kaiser et al. | 260/396 |
| 3,806,469 | 4/1974 | Morita et al. | 252/432 |
| 3,870,731 | 3/1975 | Hutchings | 260/396 |
| 3,872,134 | 3/1975 | Wistuba et al. | 260/369 |
| 3,897,464 | 7/1975 | Morgenstern et al. | 260/346.4 |
| 3,927,040 | 12/1975 | Andreikov et al. | 260/346.4 |
| 4,002,653 | 1/1977 | Reuter et al. | 260/369 |
| 4,032,548 | 6/1977 | Martin et al. | 260/396 |
| 4,035,399 | 7/1977 | Yokoyama et al. | 260/396 R |

FOREIGN PATENT DOCUMENTS 50-126588 10/1975 Japan .

OTHER PUBLICATIONS

Katzer et al.–*Ind. Chem., Process Des. Develop.,* 12(4), pp. 477–481 (1973).
Bonchev et al.–*Mikochim. Acta,* (1), pp. 116–124, (1967).
Kagarlitskii–*Neftekhim. Akad. Nauk. Turkm. SSR,* pp. 253–263 (1963).
Underwood et al.–*Org. Syntheses 16,* pp. 73–74 (1936).
Yatsimirskii et al.–*Zh. Fiz. Ihim. 44(5),* pp. 1129–1136 (1970).

*Primary Examiner*—John F. Niebling
*Attorney, Agent, or Firm*—A. J. Young

[57] ABSTRACT

A catalyst for the oxidation of phenols to 1,4-benzoquinones in the gas phase with an oxygen containing gas such as air, substantially pure oxygen, or mixtures thereof. The composition of the catalyst comprises vanadium pentoxide or ammonium metavanadate, the sulfate salt of an alkali metal or of ammonia, the pyrosulfate salt of an alkali metal or of ammonia, an iron sulfate, boric acid, and silica.

7 Claims, No Drawings

CATALYTIC OXIDATION OF PHENOLS TO 1,4-BENZOQUINONES

BACKGROUND OF THE INVENTION

This invention relates to the catalytic oxidation of phenols to 1,4-benzoquinones. More particularly, the invention relates to catalyst compositions for the oxidation of phenols to 1,4-benzoquinones in the gas phase with oxygen.

The compound 1,4-benzoquinone is beneficially used as an oxidizing and tanning agent. Moreover, 1,4-quinones are useful intermediates for making hydroquinones, which find utility as antioxidants, reducing agents, and polymer intermediates.

Benzoquinones are usually manufactured from the corresponding phenols by treating the phenols with oxidizing agents. For example, phenol may be oxidized using sodium dichromate in an aqueous sulfuric acid medium. Such methods, however, have the disadvantage that they produce solid metal oxides as by-products and require stoichiometric amounts of the oxidant. An additional disadvantage is that the benzoquinone products formed are mixed with other compounds and must be separated to obtain a substantially pure form thereof.

It is desirable to have a commercial process which may be used to manufacture benoquinones in significant yield and with a high degree of purity by a direct catalytic oxidation of the corresponding phenols. While it is known that phenols can be oxidized directly to the corresponding benzoquinones in the presence of a copper-containing catalyst, the process is carried out in solution, with the inherent problem of separating the products from the solvent and recycling of the catalyst. The present invention provides a heterogeneous catalyst for the oxidation of phenols to the corresponding benzoquinones in the gas phase, thereby eliminating the problem of solvent-product separation and catalyst recycle.

SUMMARY

In general, this invention provides a heterogeneous catalyst for the oxidation of phenol and substituted phenols to the corresponding 1,4-benzouinones in the gas phase with oxygen. The composition of the catalyst comprises vanadium pentoxide or ammonium metavanadate, and ammonium or alkali-metal sulfate, an ammonium or alkali-metal pyrosulfate, ferrous or frerric sulfate, boric acid, and silica. As used herein, the term "silica" is defined as any compound which is predominately silican dioxide and which may include up to about ten percent water by weight.

It is an object of the present invention to provide a catalyst for the oxidation of phenols to the corresponding 1,4-benzoquinones. It is a further object of this invention to provide a heterogeneous catalyst for the gas-phase oxidation of phenols to the corresponding 1,4-benzoquinones. It is a still further object of the invention to provide a catalyst which is active in promoting the oxidation of phenols to 1,4-benzoquinones at a relatively rapid rate. It is a still further object of the invention to provide a catalyst which selectively promotes the oxidation of phenols to 1,4-benzoquinones and concomitantly reduces the proportion of other reaction products. It is a still further object of the invention to provide a catalyst which greatly simplifies the recovery of the desired products from the reaction mixtures. These and other objects of this invention will be apparent to those skilled in the art from the more detailed description which follows.

DESCRIPTION OF THE PREFERRED EMBODIMENTS

The following description illustrates the manner in which the principles of the present invention are applied, but is not to be construed as in any sense limiting the scope of the invention.

The catalyst composition may include a binder which is preferably a cellulose ether. More preferably, the binder is a hydroxyalkylalkylcellulose ether and, most preferably, is a hydroxypropylmethylcellulose ether.

The composition of the catalyst comprises between about sixty and about eighty-five parts by weight of vanadium pentoxide as $V_2O_5$ or equivalent amount of ammonium metavanadate, between about one hundred and about one hundred and fifty parts by weight of potassium sulfate as $K_2SO_4$ or equivalent amounts of sodium or ammonium sulfate, between about seventy-five and about one hundred and twenty parts by weight of ammonium pyrosulfate as $(NH_4)_2S_2O_7$ or equivalent amounts of sodium or potassium pyrosulfate, between about sixty and about one hundred parts by weight of ferrous sulfate as $FeSO_4$ or equivalent amounts of ferric sulfate, between about thirty and about fifty parts by weight of boric acid as $H_3BO_3$, between about one hundred and sixty and about two hundred and forty parts by weight of silica as $SiO_2$, and between about two and about six parts by weight of a hydroxypropylmethylcellulose ether.

More preferably the catalyst composition comprises between about seventy and about eighty parts by weight of vanadium pentoxide or equivalent amounts of ammonium metavanadate, between about one hundred and fifteen and about one hundred and thirty-five parts by weight of potassium sulfate or equivalent amounts of sodium or ammonium sulfate, between about eighty and about one hundred parts by weight of ammonium pyrosulfate or equivalent amounts of sodium or potassium pyrosulfate, between about seventy and about ninety parts by weight of ferrous sulfate or equivalent amounts of ferric sulfate, between about thirty-five and about forty-five parts by weight of boric acid, between about one hundred and eighty and about two hundred and twenty parts by weight of silica, and between about three and about five parts by weight of the hydroxypropylmethylcellulose ether.

The components of the catalyst mixture may be used without special blending techniques. However, the preferred embodiment includes thorough mixing of the components. Preferably, the mixing step is carried out on a two-roll mill. The final preferred step of preparing the catalyst being the pressing of the catalyst into dry pellets. Catalysts prepared as described above are highly useful for the catalytic oxidation of phenols to 1,4-benzoquinones in the gas phase. The oxidizing agent is oxygen and is provided by any oxygen containing gas such as air. The reaction temperature is between about 200° C. and about 600° C. and is preferably between about 300° C. and about 500° C.

Substituted phenols which may be useful for oxidation according to the present invention include 2,6-ditertiary-butyl phenol, 2-tertiary-butyl phenol, ortho-chlorophenol, ortho-phenyl phenol, ortho-benzol phenol, 2,6-dichlorophenol, ortho-vinyl phenol, and ortho-cresol.

The principles of this invention will now be illustrated by the following examples. It is to be understood, however, that these examples are illustrative only, and are by no means to be construed as in any way limiting the scope of the invention.

EXAMPLE 1

An active catalyst for the vapor-phase oxidation of phenols to 1,4-benzoquiniones was prepared by mixing, about two hours on a two-roll, seventy-three grams of vanadium pentoxide ($V_2O_5$), one hundred and twenty-four grams of potassium sulfate ($K_2SO_4$), ninety-four grams of ammonium pyrosulfate [$(NH_4)_2S_2O_7$], eighty grams of ferrous sulfate ($FeSO_4$), forty grams of boric acid ($H_3BO_3$), and two hundred grams of silica ($SiO_2$). About two hundred milliliters of a two percent by weight aqueous solution of a hydroxypropylmethylcellulose ether was added as a binder to the catalyst mixture from which pellets were formed. The pellets were then dried at 100° C. for about two hours.

EXAMPLE 2

An oxidizing gas mixture comprising two parts of nitrogen and one part of air by volume was preheated to 175° C. and used to transport phenol vapors from a heated vaporizer (150° C.) containing phenol through a heated catalyst bed. The catalyst used was that prepared in Example 1. The space velocity of the oxidizing gas and phenol mixture through the catalyst bed was nine hundred and forty-two reciprocal hours. The produce mixture was condensed in two air-cooled flasks and an ice-cooled trap which contained acetone, the vessels being connected in series. The condensed samples were weighed, then analyzed by gas chromatography.

The results of these gas-phase oxidation experiments are tabulated in Table 1 below.

TABLE 1

| Catalyst Temp. (°C.) | Composition of Product Mixture (Mole %) | | Conversion (%) | Selectivity to 1,4-Benzoquinone (%) |
|---|---|---|---|---|
| | Phenol | 1,4-Benzoquinone | | |
| 325 | 49.1 | 8.6 | 51 | 16.8 |
| 350 | 52.8 | 5.3 | 47 | 11.3 |
| 375 | 54.4 | 6.5 | 46 | 14.2 |
| 400 | 55.3 | 11.6 | 45 | 26.0 |
| 425 | 66.1 | 18.4 | 34 | 54.4 |
| 450 | 49.8 | 9.0 | 50 | 18.0 |

The data indicate that the reaction became more selective to 1,4-benzoquinone as the conversion of phenol deceased. The highest selectivity, 54.4 percent, was obtained at the lowest conversion, 34 percent. This trend would be expected to continue if the experimental conditions were changed to obtain conversions below thirty-four percent.

While certain representative embodiments and details have been shown for the purpose of illustrating this invention, it will be apparent to those skilled in the art that various changes and modifications can be made therein without departing from the spirit and scope of the invention. For example, mixed salts such as ferrous ammonium sulfate may be used instead of or in addition to ferrous sulfate, potassium sulfate, or ammonium sulfate; borax instead of or in addition to boric acid; and silicic acid instead of or in addition to silica.

What is claimed is:

1. A heterogeneous catalyst for the oxidation of phenol and substituted phenols to the corresponding 1,4-benzoquinones in the gas phase, the composition of the catalyst comprising a mixture of vanadium pentoxide or ammonium metavanadate, an ammonium or alkali-metal sulfate, an ammonium or alkali-metal pyrosulfate, ferrous or ferric sulfate, boric acid, and silica.

2. The catalyst of claim 1, wherein the catalyst includes a binder.

3. The catalyst of claim 2, wherein the binder is a cellulose ether.

4. The catalyst of claim 3, wherein the binder is a hydroxyalkylalkylcellulose ether.

5. The catalyst of claim 4, wherein the binder is a hydroxypropylmethylcellulose ether.

6. The catalyst of claim 5, wherein the mixture comprises between about sixty and about eighty-five parts by weight of vanadium pentoxide or equivalent amounts of ammonium metavanadate, between about one hundred and about one hundred and fifty parts by weight of potassium sulfate or equivalent amounts of sodium or ammonium sulfate, between about seventy-five and about one hundred and twenty parts by weight of ammonium pyrosulfate or equivalent amounts of sodium or potassium pyrosulfate, between about sixty and about one hundred parts by weight of ferrous sulfate or equivalent amounts of ferric sulfate, between about thirty and about fifty parts by weight of boric acid, between about one hundred and sixty and about two hundred and forty parts by weight of silica, and between about two and about six parts by weight of the hydroxypropylmethylcellulose ether.

7. The catalyst of claim 6, wherein the mixture comprises between about seventy and about eighty parts by weight of vanadium pentoxide or equivalent amounts of ammonium metavanadate, between about one hundred and fifteen and about one hundred and thirty-five parts by weight of potassium sulfate or equivalent amounts of sodium or ammonium sulfate, between about eighty and about one hundred parts by weight of ammonium pyrosulfate or equivalent amounts of sodium or potassium pyrosulfate, between about seventy and about ninety parts by weight of ferrous sulfate or equivalent amounts of ferric sulfate, between about thirty-five and about forty-five parts by weight of boric acid, between about one hundred and eighty and about two hundred and twenty parts by weight of silica, and between about three and about five parts by weight of the hydroxypropylmethylcellulose ether.

* * * * *